US012667599B2

(12) United States Patent
Lee et al.

(10) Patent No.: US 12,667,599 B2
(45) Date of Patent: Jun. 30, 2026

(54) PHARMACEUTICAL COMPOSITION OR HEALTH FUNCTIONAL FOOD FOR PREVENTION AND TREATMENT OF OBESITY CONTAINING POWDER OF NOVEL HYBRID MUSHROOM AS ACTIVE INGREDIENT

(71) Applicant: Novacell Technology Inc., Gyeongsangbuk-do (KR)

(72) Inventors: Tae Hoon Lee, Seoul (KR); Jae Wang Ghim, Gyeongsangbuk-do (KR)

(73) Assignees: Novacell Technology Inc., Pohang-si (KR); Gyongsangbuk-do, Andong-si (KR)

( * ) Notice: Subject to any disclaimer, the term of this patent is extended or adjusted under 35 U.S.C. 154(b) by 603 days.

(21) Appl. No.: 18/090,898

(22) Filed: Dec. 29, 2022

(65) Prior Publication Data

US 2023/0146268 A1 May 11, 2023

Related U.S. Application Data

(63) Continuation-in-part of application No. PCT/KR2021/007554, filed on Jun. 16, 2021.

(30) Foreign Application Priority Data

Jun. 29, 2020 (KR) ........................ 10-2020-0079171

(51) Int. Cl.

| | |
|---|---|
| *A61K 36/07* | (2006.01) |
| *A23L 33/00* | (2016.01) |
| *A23L 33/10* | (2016.01) |
| *A61P 1/16* | (2006.01) |
| *A61P 3/04* | (2006.01) |

(52) U.S. Cl.
CPC .............. *A61K 36/07* (2013.01); *A23L 33/10* (2016.08); *A23L 33/30* (2016.08); *A61P 1/16* (2018.01); *A61P 3/04* (2018.01)

(58) Field of Classification Search
None
See application file for complete search history.

(56) References Cited

U.S. PATENT DOCUMENTS

2017/0368133 A1 12/2017 Schwartz et al.

FOREIGN PATENT DOCUMENTS

| | | | |
|---|---|---|---|
| CN | 107549819 A | 1/2018 |
| KR | 1020160141027 A | 12/2016 |
| KR | 1020170000603 U | 1/2017 |
| KR | 101780941 B1 | 5/2017 |
| KR | 102074058 B1 | 8/2019 |
| KR | 1020190098685 A | 8/2019 |

OTHER PUBLICATIONS

Woo (KR 20190100711—English translation) Aug. 29, 2019.*
Alam et al., "Dietary effect of Pleurotus eryngii on biochemical function and histology in hypercholesterolemic rats," Saudi Journal of Biological Sciences (2011) 18, 403-409 , Jul. 26, 2011.
Brunner et al., "Nonalcoholic Fatty Liver Disease and Obesity Treatment," Curr Obes Re. Sep. 2019, pp. 220-228.
EP Extended European Search Report cited in the International Application No. PCT/KR2021007554, mailed on Aug. 27, 2024.
International Search Report and Written Opinion for International Application No. PCT/KR2021/007554 dated Oct. 14, 2021, with English language translation of ISR.

* cited by examiner

*Primary Examiner* — Susan Hoffman
(74) *Attorney, Agent, or Firm* — Potomac Law Group, PLLC; Judith U. Kim

(57) ABSTRACT

The present invention provides a pharmaceutical composition for the treatment of obesity and fatty liver disease caused due to a high-fat diet, containing, as an active ingredient, the powder of a fruiting body or a mycelium of hybrid mushroom strain GBN2WP0970 having no side effects and an excellent triglyceride absorption inhibitory effect.

6 Claims, 4 Drawing Sheets

PHARMACEUTICAL COMPOSITION OR HEALTH FUNCTIONAL FOOD FOR PREVENTION AND TREATMENT OF OBESITY CONTAINING POWDER OF NOVEL HYBRID MUSHROOM AS ACTIVE INGREDIENT

CROSS-REFERENCE TO RELATED APPLICATIONS

This application is a continuation-in-part of PCT/KR2021/007554, having an international filing date of Jun. 16, 2021, which claims priority to KR 10-2020-0079171, having a filing date of Jun. 29, 2020, and both applications are incorporated herein by reference in their entirety.

TECHNICAL FIELD

The present invention relates to a pharmaceutical composition for the prevention and treatment of obesity containing powder of a novel hybrid mushroom as an active ingredient, and more specifically a pharmaceutical composition for the prevention and treatment of obesity containing, as an active ingredient, powder of a novel hybrid mushroom having a high neutral fat inhibition rate.

BACKGROUND ART

Because of the recent improvement in living standards due to economic development, modern people can enjoy a rich diet, but changes in dietary life to a meat-based diet caused excessive intake of calories. These changes in the dietary life of modern people tend to rapidly increase the number of obese people because they consume less heat due to insufficient exercise. Obesity is caused by an imbalance between the intake and consumption of energy, and excess energy is converted into the form of adipocytes and stored in the body. There are about 20 billion adipocytes in the human body, which are responsible for accumulating or releasing energy in the mammals' living bodies, and the adipocytes store, in the form of neutral fat, the energy remaining after consumed and then decompose it into free fatty acids and glucose when the energy is depleted. Due to this imbalance in the storage and decomposition process, when excessive energy is accumulated, the number or size of adipocytes increases, resulting in obesity. Fatty liver refers to a non-health condition that explains the case when the fat content of human liver is greater than 5% and is known to be caused by several complex causes, but the fatty liver can be divided into alcoholic fatty liver due to excessive drinking and non-alcoholic fatty liver associated with other causes of disease unrelated to alcohol. Among them, alcoholic fatty liver (alcoholic steatohepatitis, ASH), which is fatty liver caused by drinking, is one of liver diseases, the second most serious diseases after cancer among the causes of death among adults in their 40s and 50s in advanced countries, and unlike the alcoholic fatty liver which is directly related to alcohol, non-alcoholic fatty liver (non-alcoholic steatohepatitis, NASH) refers to a disease in which neutral fats accumulate in the liver regardless of drinking, clinically is recognized as a progressive liver disease and a preceding disease that causes cirrhosis or liver cancer, which is very meaningful. In this regard, Korean Patent Publication No. 2019-0098685 discloses a pharmaceutical composition for treating a fatty liver disease and a health functional food for improving liver function comprising extracts or powder of *Pleurotus eryngii* var. *ferulea* (Pf.).

DISCLOSURE OF THE INVENTION

Technical Problem

However, the related art uses the extract or powder of *Pleurotus eryngii* var. *ferulea* (Pf.), and there is no research on the use of a new variety of mushrooms for the treatment of obesity and fatty liver disease by the hybridization breeding of *Pleurotus eryngii* var. *ferulea* (Pf.) and *Pleurotus ostreatus*.

The purpose of the present invention is to provide a pharmaceutical composition for the prevention and treatment of obesity, the pharmaceutical composition containing, as an active ingredient, the powder of a novel hybrid mushroom having no side effects and excellent effects of inhibiting the absorption of neutral fat. However, this problem is exemplary, and the scope of the present invention is not limited thereto.

Technical Solution

According to an aspect of the present invention, there is provided a method for treating fatty liver disease due to a high-fat diet in a subject, comprising administering a therapeutically effective amount of powder of a fruiting body or a mycelium of hybrid mushroom *Pleurotus* sp. GBN2WP0970 to the subject.

According to another aspect of the present invention, there is provided a method for treating obesity due to a high-fat diet in a subject, comprising administering a therapeutically effective amount of powder of a fruiting body or a mycelium of hybrid mushroom *Pleurotus* sp. GBN2WP0970 to the subject.

Advantageous Effects

Because it has been confirmed that the pharmaceutical composition for the treatment of obesity and fatty liver disease, the pharmaceutical composition containing, as an active ingredient, the powder of the novel hybrid mushroom as described above has an excellent effect of inhibiting neutral fat absorption using the hybrid mushroom selected through the hybridization of conventional mushrooms having various functions, the pharmaceutical composition may be utilized as a material for a drug, a functional health food, and a general food for the prevention or treatment of obesity. However, the scope of the present invention is not limited by such an effect.

BEST MODE FOR CARRYING OUT THE INVENTION

Definition of Terms

Figure 1:
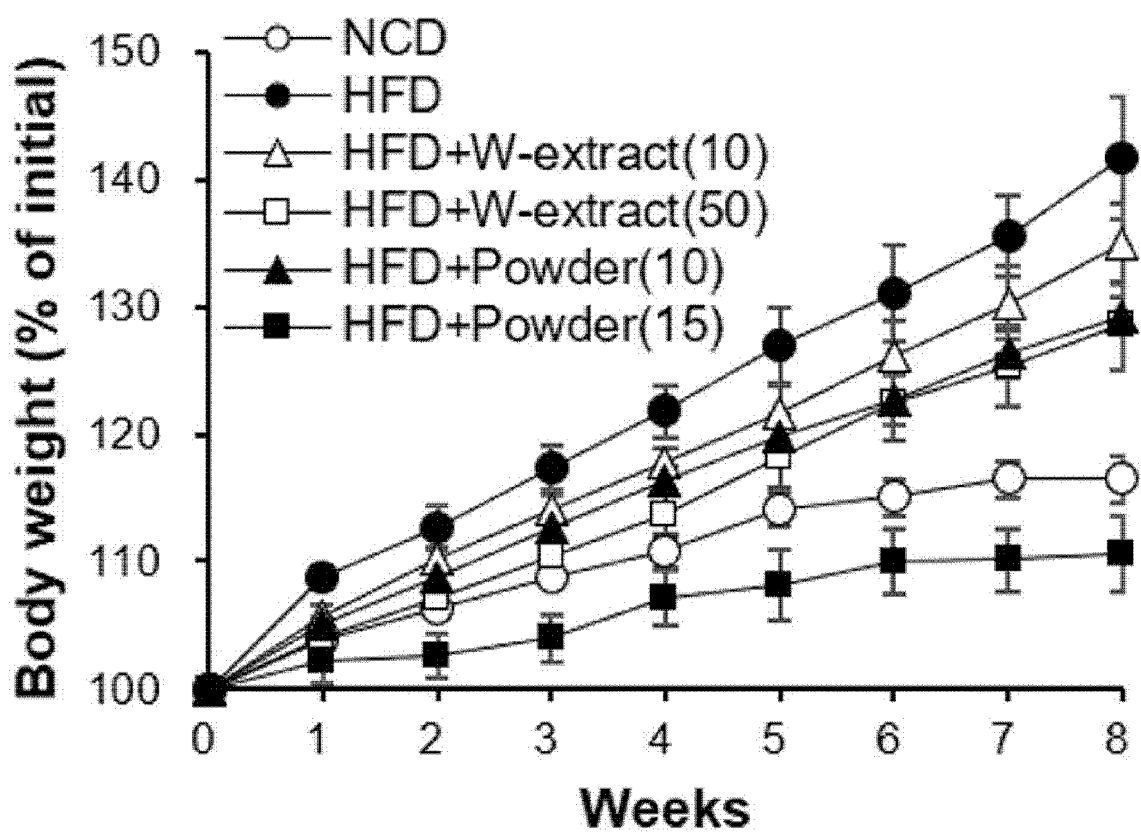
FIG. 1 is a graph obtained by analyzing changes in body weight after administering, to an experimental animal, the powder and water extract of a novel hybrid mushroom of the present invention.

As used herein, the term "novel hybrid mushroom" refers to a mushroom cultivated by novel *Pleurotus* sp. GBN2WP0970 generated by crossbreeding of *Pleurotus eryngii* var. *ferulea* (Pf.) and *Pleurotus ostreatus* (Korean Patent Publication No. 2019-0100711).

As used herein, the term "non-alcoholic fatty liver (non-alcoholic steatohepatitis, NASH)" refers to a disease in which neutral fat accumulates in the liver according to genetic, environmental, and lifestyle causes regardless of drinking, and is clinically recognized as a progressive liver and a preceding disease that causes cirrhosis or liver cancer, which is very meaningful. There are various causes, but major adult diseases such as obesity, insulin-resistant diabetes, and hyperlipidemia are recognized as risk factors.

As used herein, the term "fruiting body" refers to propagative organs of mushrooms and corresponds to flowers of ordinary plants. The fruiting body is the multicellular structure for the sexual reproduction of fungi, and the mushrooms people eat refer to this fruiting body. The mycelium accumulates enough nutrients, then grows at once, and becomes a visible fruiting body if the climatic conditions are satisfied.

As used herein, the term "mycelium" is a vegetative organ of a mushroom, is the parent of a fungus that looks like white downy hair or thread, and corresponds to the roots, stems, and leaves of general plants. Most of the mushroom life is parasitic or saprophytic in a state of mycelium. The mycelium is known to have four times higher nutrients and medicinal ingredients than the fruiting body.

DETAILED DESCRIPTION OF THE INVENTION

According to an aspect of the present invention, there is provided a method for treating fatty liver disease due to a high-fat diet in a subject, comprising administering a therapeutically effective amount of powder of a fruiting body or a mycelium of hybrid mushroom *Pleurotus* sp. GBN2WP0970 to the subject.

In the method, the hybrid mushroom *Pleurotus* sp. GBN2WP0970 may be generated by crossbreeding of *Pleurotus eryngii* var. *ferulea* (Pf.) and *Pleurotus ostreatus*.

In the method, the fatty liver disease may be alcoholic fatty liver disease or non-alcoholic fatty liver disease, and the non-alcoholic fatty liver disease may be non-alcoholic fatty liver, non-alcoholic steatohepatitis, or non-alcoholic fatty liver-related cirrhosis.

According to another aspect of the present invention, there is provided a method for treating obesity due to a high-fat diet in a subject, comprising administering a therapeutically effective amount of powder of a fruiting body or a mycelium of hybrid mushroom *Pleurotus* sp. GBN2WP0970 to the subject.

In the method, the hybrid mushroom *Pleurotus* sp. GBN2WP0970 may be generated by crossbreeding of *Pleurotus eryngii* var. *ferulea* (Pf.) and *Pleurotus ostreatus*.

The novel hybrid mushroom *Pleurotus* sp. GBN2WP0970 and a fruiting body thereof (Korean Patent No. 2074058), which have a high inhibition rate of neutral fat absorption, are known as the prior art of the present invention, but the effect of inhibiting neutral fat of the water extract of the novel variety of mushroom strain and a fruiting body thereof is only described. Accordingly, the present inventors have prepared the powder of the fruiting body or mycelium of a new variety of mushroom through additional research on the obesity relief efficacy of the new variety of mushroom, and then administered the powder to a high fat fed murine animal model, thereby exhibiting excellent obesity relief efficacy, such as remarkably reducing weight gain and exhibiting a high effect of inhibiting neutral fat absorption compared to the water extract, and thus have completed the present invention based on this.

Hereinafter, the present invention will be described in more detail with reference to Examples. However, the present invention is not limited to the Examples described below, but may be implemented in various other forms, and the Examples below are provided to complete the disclosure of the present invention and to fully convey the scope of the invention to those skilled in the art.

EXAMPLES

Example 1: Preparation of Dried Powder of Novel Hybrid Mushroom

A fruiting body of a novel hybrid mushroom (GBN2WP0970) was cut into slices or pieces, and then subjected to hot-air or cold-air drying to prepare dried mushrooms whose weight was reduced to about $1/10$. Thereafter, the dried mushrooms were pulverized using a crusher or a speed mill, and the prepared powder was used to prepare an extract or directly administered to an animal model.

Example 2: Preparation of Water Extract of Novel Hybrid Mushroom

The powder of the novel hybrid mushroom prepared in Example 1 was put in an extraction container, 50 mL of water was mixed as an extraction solvent per 1 g of powder, and then extraction was performed with a shaking incubator at 37° C. for 24 hours. The supernatant in the shaking incubator obtained by centrifugation at 2,500 rpm for 10 minutes and filtering was collected and used as a testing material.

Example 3: Preparation of Experimental Animal Model

In order to observe the efficacy of relieving obesity and fatty liver of the powder and water extract of the new hybrid mushroom prepared in Example 1, an animal model of obesity was prepared by supplying a high-fat diet to mice. Specifically, after C57BL/6-line 8-week-old male mice were accustomed for 1 week with solid feed, experimental groups were formed by dividing the mice having an average weight of 22-24 g by 6 or more mice according to a randomized block design. The experimental groups were divided into a normal diet group (NCD), a high-fat diet group (HFD), a group fed with high-fat diet and the powder of the new hybrid mushroom (Powder), and a group fed with high-fat diet and the water extract of the new hybrid mushroom (W-extract). The normal diet group (NCD) was supplied with general meals in which 10% of total calories were fat, and the high-fat diet group (HFD) was supplied with foods in which 60% of total calories were fat. The group fed with high-fat diet and the powder of the new hybrid mushroom (Powder) or the water extract (W-extract) was supplied by mixing the high-fat diet and the powder or water extract of the novel hybrid mushroom according to the dose. Based on a daily high-fat diet intake of 2.5 g/head, for the group fed with the powder of the novel hybrid mushroom powder (Power) the powder of the novel hybrid mushroom was blended so that the administration amount was 10 and 15 mg/head/day, and for the group fed with the water extract of the novel hybrid mushroom (W-extract), the water extract of the novel hybrid mushroom was blended so that the intake amount (based on the powder amount obtained from the extract) was 10 and 50 mg/head/day, and the difference in calories and weight according to the blending was corrected by mixing casein. During the breeding period, water and feed were ad libitum, the animal breeding room temperature was maintained at 22±1° C., and the lighting was adjusted to a 12-hour cycle (08:00-20:00).

Experimental Example 1: Body Weight and Median Effective Dose

The present inventors observed body weight change trends by measuring body weight for 8 weeks at a predetermined time once a week in order to check the obesity relief effect of the powder and water extract of the novel hybrid mushroom of the present invention, and there was no significant difference in food intake between groups.

As a result, the group fed with the powder of the new hybrid mushroom exhibited about 50% weight loss effect from 10 mg/head/day (Powder (10)) compared to the high-fat diet group (HFD), and exhibited a lower weight than the normal diet group (NCD) when administered 15 mg/head/day (Powder (15)). On the other hand, the group fed with the water extract of the new hybrid mushroom exhibited insignificant effect when administered 10 mg/head/day (W-extract(10)), and exhibited about 50% weight loss effect compared to the high-fat diet group (HFD) when administered 50 mg/head/day (W-extract(50)) (FIG. 1).

Figure 2:
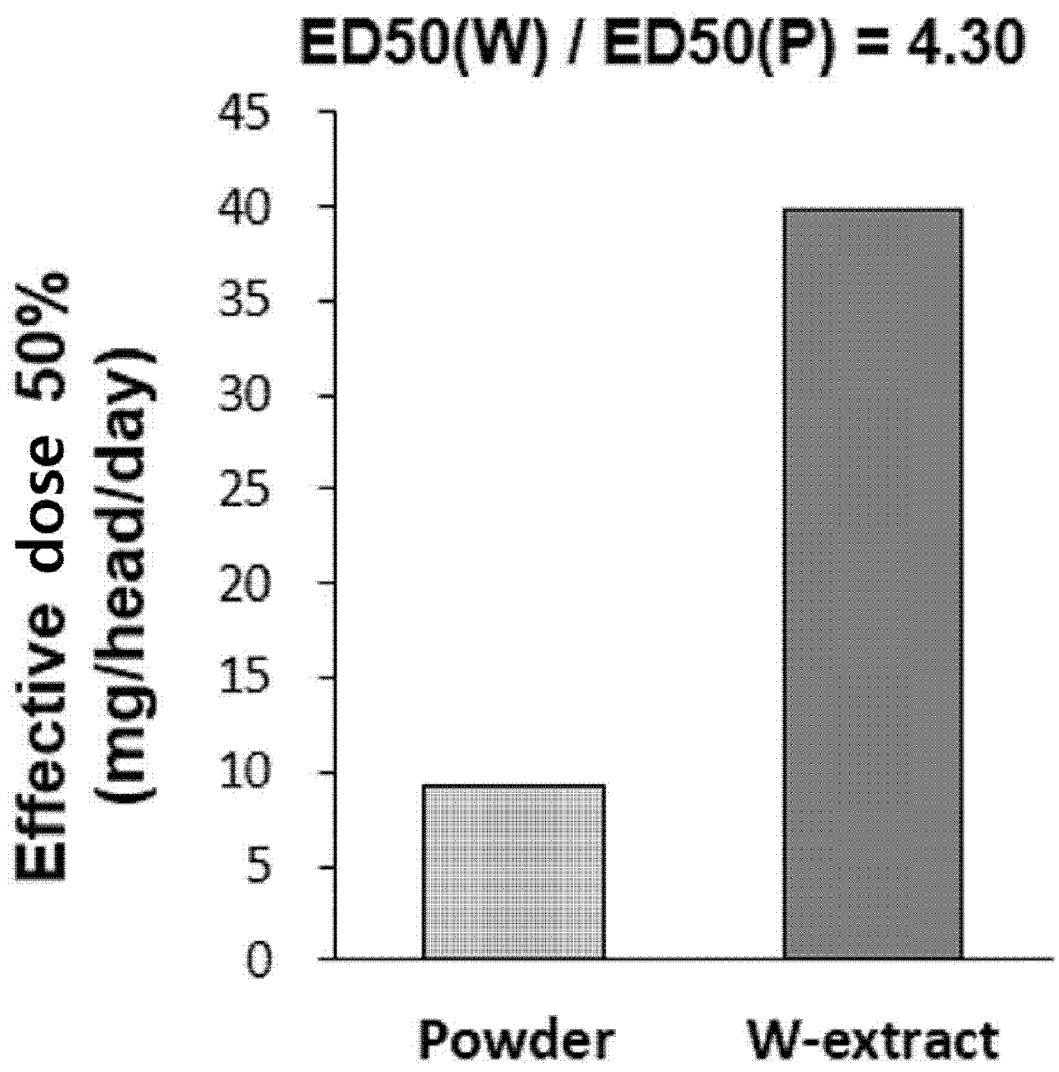
FIG. 2 is a graph obtained by analyzing the effective dose 50% after administering, to an experimental animal, the powder and water extract of a novel hybrid mushroom of the present invention.

In addition, as a result of analyzing the median effective dose (Effective dose 50%) for the obesity-relief effect of the powder and water extract of the novel hybrid mushroom of the present invention, the median effective dose (ED50(P)) of the group fed with the powder (Powder) was 9.3 mg/head/day, and that of the group fed with the water extract (W-extract) was 39.9 mg/head/day (FIG. 2). The above results mean that the powder of the novel hybrid mushroom may exhibit the same effect even with doses 4.3 times less than those of the water extract.

Experimental Example 2: Analysis of Changes in Size of Adipocytes

The present inventors analyzed the change in size of the adipose tissue, which is a major metabolic tissue, in order to compare and evaluate the obesity-relief effect of the powder and water extract of the novel hybrid mushroom of the present invention. Specifically, after the 8-week anti-obesity effect experiment of Experimental Example 1 was completed, mice in the normal diet group (NCD), the high-fat diet group (HFD), the group fed with the powder of the novel hybrid mushroom (Powder (15)), and the group fed with the water extract (W-extract (50)) were sacrificed, and then epididymal white adipose tissue was extracted and fixed in a 4% paraformaldehyde solution for tissue analysis. Thereafter, a 4-μm tissue section was prepared through ethanol dehydration and paraffin embedding process, and stained with hepatoxyin & eosin method, and then tissue image was observed under a microscope.

Figure 3:
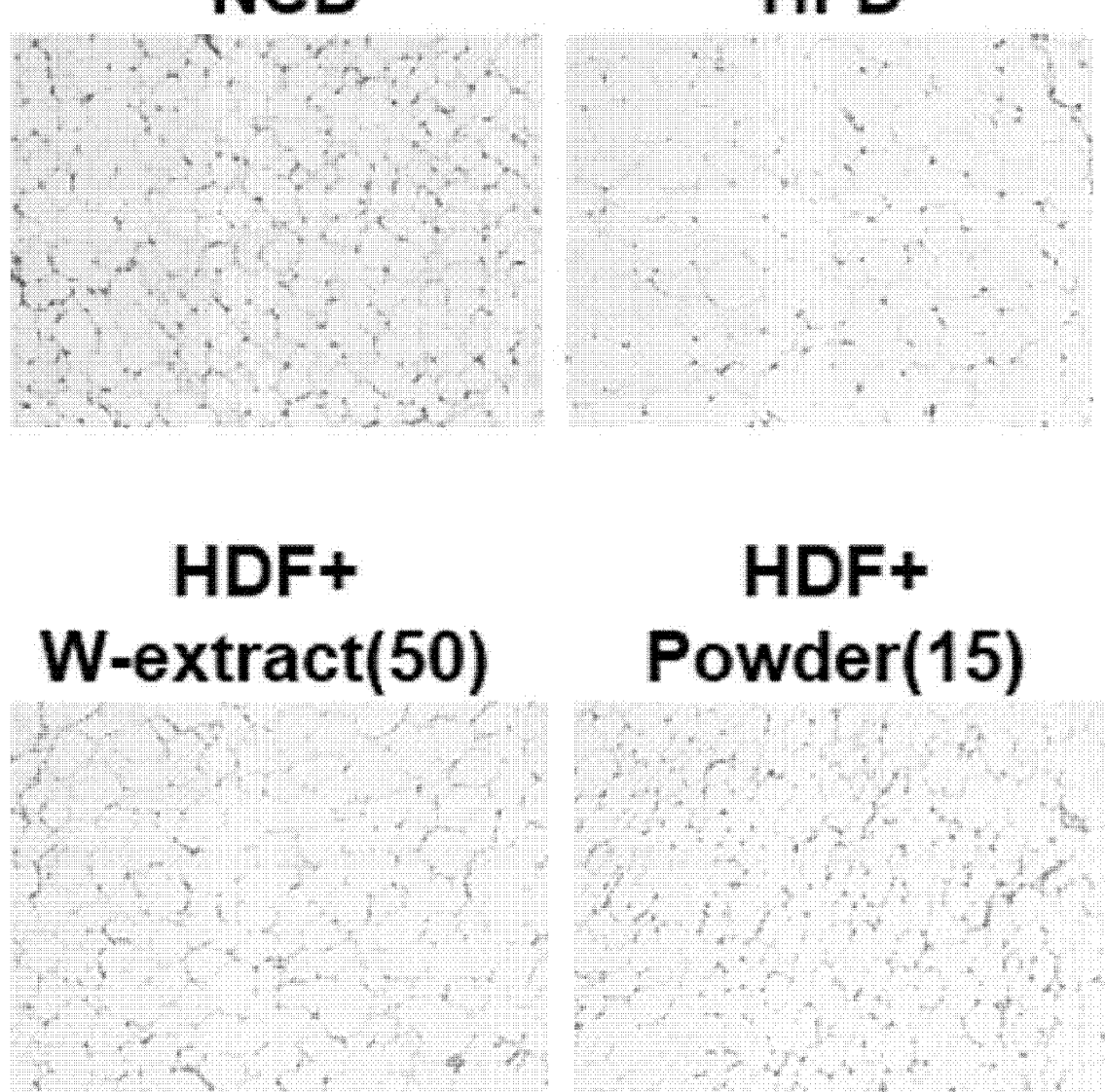
FIG. 3 is a microscope photograph obtained by observing changes in the size of adipose tissue after administering, to an experimental animal, the powder and water extract of a novel hybrid mushroom of the present invention.

As a result, the cells of adipose tissue in the high-fat diet group (HFD) were very large due to fat accumulation, and the group fed with 15 mg/head/day of the powder of the novel hybrid mushroom (Powder (15)) exhibited a smaller adipocyte size compared to the normal diet group (NCD). On the other hand, the group fed with 50 mg/head/day of the water extract of the novel hybrid mushroom (W-extract (50)) exhibited insignificant effect despite doses about 3.3 times more than those of the powder (FIG. 3).

Experimental Example 3: Measurement of Liver Tissue Weight

The present inventors extracted the liver tissues of the experimental animals in Experimental Example 1 and analyzed changes in the weight and fat accumulation of the liver tissues. Specifically, mice in the normal diet group (NCD), the high-fat diet group (HFD), the group fed with the powder of the novel hybrid mushroom (Powder (15)), and the group fed with the water extract (W-extract (50)) in which the body weight had been measured in Experimental Example 1 were sacrificed to extract liver tissues and then the weights thereof were measured.

Figure 4:
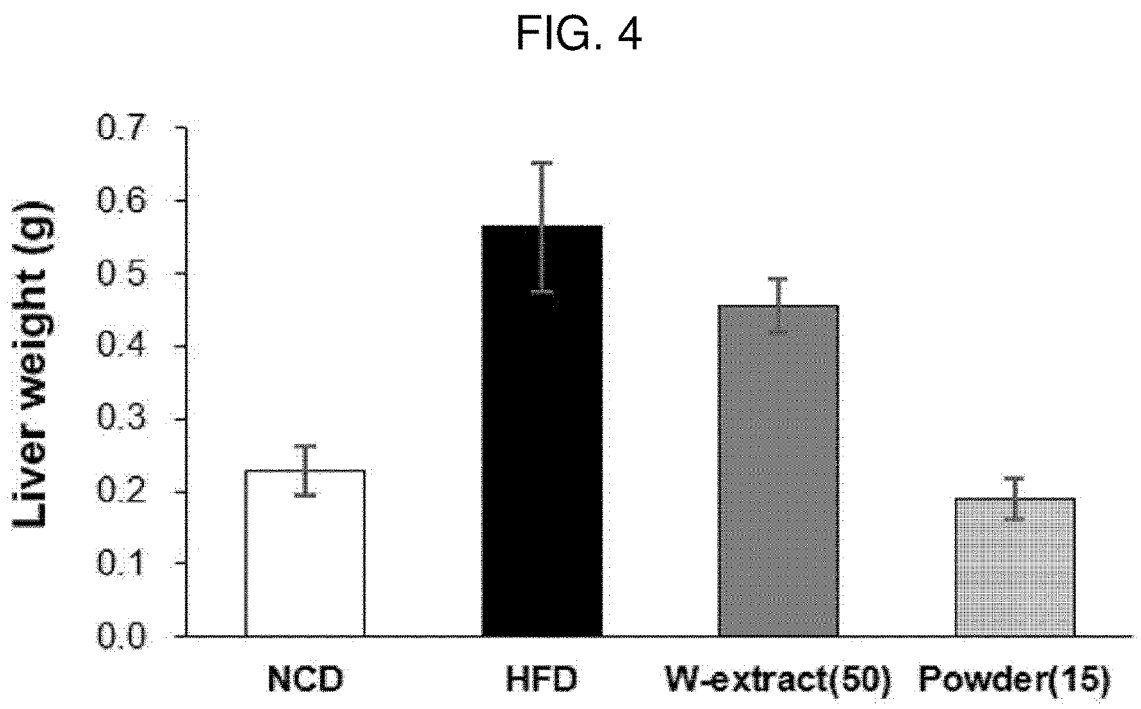
FIG. 4 is a graph obtained by analyzing the weight of liver tissue after administering, to an experimental animal, the powder of a novel hybrid mushroom of the present invention.

As a result, the group fed with 15 mg/head/day of the powder of the novel hybrid mushroom (Powder (15)) of the present invention exhibited a liver tissue weight similar to that of the normal diet group (NCD), but the group fed with 50 mg/head/day of the water extract (W-extract (50)) exhibited a slightly lower reduction effect than the high-fat diet group (HFD) even though the amount of the water extract was administered in a larger amount than the powder (FIG. 4).

Experimental Example 4: Analysis of Changes in Fat Accumulation

The present inventors measured the triglyceride (TG) value in the liver tissue after measuring the weight of the liver tissue in order to check whether the value of triglycerides in the liver may be reduced when the powder of the novel hybrid mushroom of the present invention is fed.

Specifically, at least 100 mg of liver tissues extracted from experimental animals were prepared, put into a 5% NP-40 solution, and homogenized. The homogenized liver tissues were slowly heated in a constant temperature bath (water bath) at 80-100° C. for about 2-5 minutes and then cooled at room temperature. Thereafter, heating and cooling were repeated so that the triglycerides in the tissue could be dissolved well. Then, the solution was centrifuged at a speed of at least 12,000 rpm for 2 minutes, and a triglyceride content was measured using a supernatant through a serum triglyceride quantitative kit (Sigma, USA).

Figure 5:
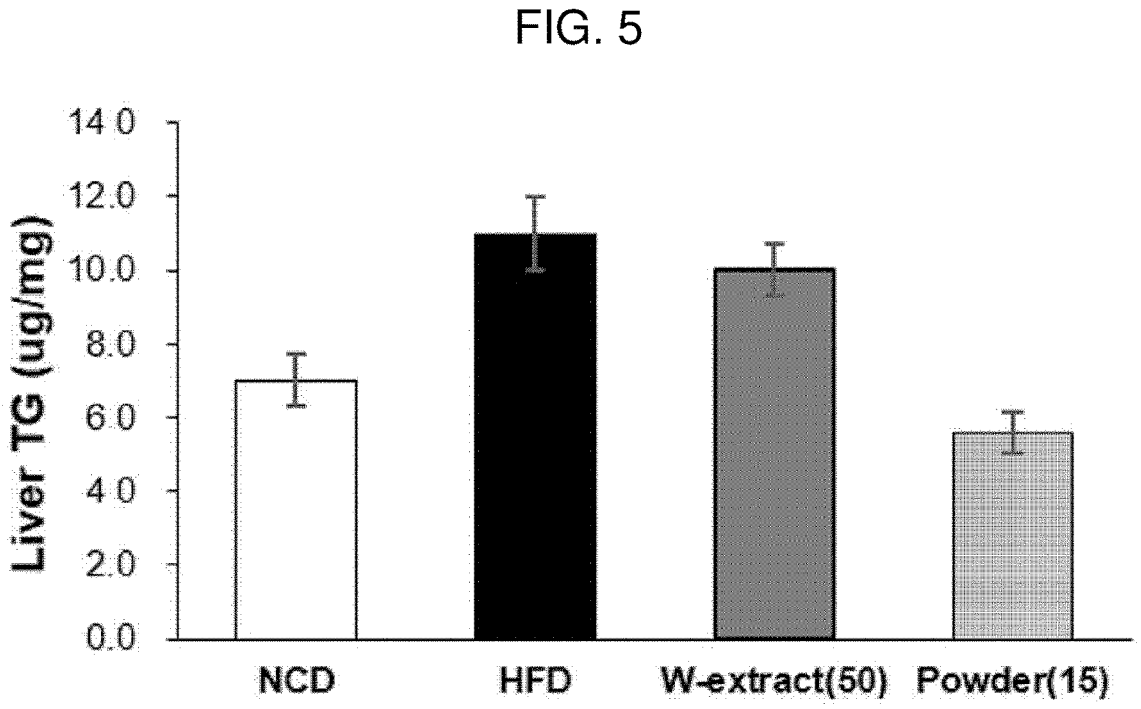
FIG. 5 is a graph obtained by analyzing triglyceride (TG) content in the liver after administering, to an experimental animal, the powder of a novel hybrid mushroom of the present invention.

As a result, it was confirmed that in the case of the high-fat diet group (HFD), the triglyceride concentration in the liver tissue was very high, but in the group fed with the powder of the novel hybrid mushroom (Powder (15)), the triglyceride concentration was reduced to the level of the normal diet group (NCD), and the effect of reducing fat accumulation in the liver was very excellent. However, the group fed with 50 mg/head/day of the water extract (W-extract (50)), in a larger amount than the powder, exhibited slightly decreased level of the triglyceride concentration than the high-fat diet group (HFD) (FIG. 5). The above results suggest that the administration of the powder of the novel hybrid mushroom of the present invention inhibits the absorption of triglyceride, thereby exhibiting an excellent anti-obesity improvement effect.

In conclusion, the pharmaceutical composition for the prevention and treatment of obesity, containing, as an active ingredient, the powder of the novel hybrid mushroom of the present invention exhibits excellent anti-obesity effects due to a triglyceride absorption inhibitory effect, and therefore can be utilized as a material for medicines for the treatment of anti-obesity and fatty liver disease, and for functional health foods.

The present invention is described with reference to the described examples, but the examples are merely illustrative. Therefore, it will be understood by those skilled in the art that various modifications and other equivalent examples can be made from the described examples. Hence, the real protective scope of the present invention shall be determined by the technical spirit of the accompanying claims.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

The invention claimed is:

1. A method for treating fatty liver disease in a subject, comprising administering a therapeutically effective amount of powder of a fruiting body or a mycelium of hybrid mushroom *Pleurotus* sp. GBN2WP0970 to the subject.

2. The method of claim 1, wherein the hybrid mushroom *Pleurotus* sp. GBN2WP0970 is generated by crossbreeding of *Pleurotus eryngii* var. *ferulea* (Pf.) and *Pleurotus ostreatus*.

3. The method of claim 1, wherein the fatty liver disease is non-alcoholic fatty liver disease.

4. The method of claim 3, wherein the non-alcoholic fatty liver disease is non-alcoholic fatty liver, non-alcoholic steatohepatitis, or non-alcoholic fatty liver-related cirrhosis.

5. A method for treating obesity in a subject, comprising administering a therapeutically effective amount of powder of a fruiting body or a mycelium of hybrid mushroom *Pleurotus* sp. GBN2WP0970 to the subject.

6. The method of claim 5, wherein the hybrid mushroom *Pleurotus* sp. GBN2WP0970 is generated by crossbreeding of *Pleurotus eryngii* var. *ferulea* (Pf.) and *Pleurotus ostreatus*.

* * * * *